US011219638B2

(12) United States Patent
Colliec-Jouault et al.

(10) Patent No.: US 11,219,638 B2
(45) Date of Patent: Jan. 11, 2022

(54) ANTI-METASTATIC MARINE BACTERIAL EXOPOLYSACCHARIDE DERIVATIVE AND USES THEREOF

(71) Applicants: INSTITUT FRANCAIS DE RECHERCHE POUR L'EXPLOITATION DE LA MER (IFREMER), Issy les Moulineaux (FR); UNIVERSITE DE NANTES, Nantes (FR); INSERM (Institut National de la Santé et de la Recherche Médicale), Paris (FR); CENTRE HOSPITALIER UNIVERSITAIRE DE NANTES, Nantes (FR)

(72) Inventors: Sylvia Colliec-Jouault, Nantes (FR); Corinne Sinquin, Nantes (FR); Jacqueline Ratiskol, Sainte Luce sur Loire (FR); Dominique Heymann, Indre (FR); Carmen Ruiz-Velasco, Marina Del Rey, CA (US); Julie Chesneau, Nantes (FR)

(73) Assignees: INSTITUT FRANCAIS DE RECHERCHE POUR L'EXPLOITATION DE LA MER (IFREMER), Issy les Moulineaux (FR); UNIVERSITE DE NANTES, Nantes (FR); INSERM (Institut National de la Santé et de la Recherche Médicale), Paris (FR); CENTRE HOSPITALIER UNIVERSITAIRE DE NANTES, Nantes (FR)

( * ) Notice: Subject to any disclaimer, the term of this patent is extended or adjusted under 35 U.S.C. 154(b) by 0 days.

(21) Appl. No.: 15/763,407

(22) PCT Filed: Sep. 28, 2016

(86) PCT No.: PCT/EP2016/073035
§ 371 (c)(1),
(2) Date: Mar. 26, 2018

(87) PCT Pub. No.: WO2017/055310
PCT Pub. Date: Apr. 6, 2017

(65) Prior Publication Data
US 2018/0280427 A1    Oct. 4, 2018

(30) Foreign Application Priority Data
Sep. 28, 2015  (EP) .................... 15187107

(51) Int. Cl.
*A61K 31/737*   (2006.01)
*A61K 35/74*    (2015.01)
*A61P 35/04*    (2006.01)

(52) U.S. Cl.
CPC .......... *A61K 31/737* (2013.01); *A61K 35/74* (2013.01); *A61P 35/04* (2018.01)

(58) Field of Classification Search
CPC ........ A61K 31/737; A61K 35/74; A61P 35/04
See application file for complete search history.

(56) References Cited

U.S. PATENT DOCUMENTS

| 7,833,990 B2 | 11/2010 | Matou et al. |
| 8,598,142 B2 * | 12/2013 | Senni ................ A61K 31/737 514/54 |
| 2007/0142323 A1 | 6/2007 | Viskov et al. |
| 2007/0259833 A1 | 11/2007 | Matou et al. |

FOREIGN PATENT DOCUMENTS

| FR | 2866650 A1 | 8/2005 |
| FR | 2871379 A1 | 12/2005 |
| FR | 2871476 A1 | 12/2005 |
| WO | WO-2006/003290 A2 | 1/2006 |

OTHER PUBLICATIONS

"prevent", WordNet Search 3.1; available at http://wordnet.princeton.edu/perl/webwn; obtained May 2019 (Year: 2019).*
Senni, K. et al., Marine Drugs, "Marine Polysaccharides: A Source of Bioactive Molecules for Cell Therapy and Tissue Engineering", 2011, vol. 9, p. 1664-1681 (Year: 2011).*
Weilbaecher, K. et al., Nature Reviews: Cancer, "Cancer to bone: a fatal attraction", Jun. 2011, vol. 11, pp. 411-425 (Year: 2011).*
Zips, D. et al., In Vivo, "New Anticancer Agents: In Vitro and In Vivo Evaluation", 2005, vol. 19, No. 1-8 (Year: 2005).*
Endo-Munoz, Liliana et al., Biochimica et Biophysica Acta, "The role of osteoclasts and tumour-associated macrophages in osteosarcoma metastasis", 2012, vol. 1826, pp. 434-442 (Year: 2012).*
International Search Report and Written Opinion, corresponding International Application No. PCT/EP2016/073035, dated Dec. 8, 2016.
Ruiz Velaso C et al., An exopolysaccharide produced by alteromonas infernus reduces lung metastasis and prolongs survival rate of osteosarcoma-bearing mice, Bone, vol. 48, No. 1, Jan. 1, 2011, pp. S42-S43.
Anthony Courtois et al: "Exopolysaccharides Isolated from Hydrothermal Vent Bacteria Can Modulate the Complement System", PLOS ONE, vol. 9, No. 4, Apr. 15, 2014, e94965, pp. 1-7.
Stevenson et al: "Heparin attenuates metastasis mainly due to inhibition of P- and L-selectin, but non-anticoagulant heparins can have additional effects", Thrombosis Research, vol. 120, Jan. 1, 2007, pp. S107-S111.

(Continued)

*Primary Examiner* — Bahar Craigo
(74) *Attorney, Agent, or Firm* — Marshall, Gerstein & Borun LLP

(57) ABSTRACT

The invention provides a low-molecular-weight (15 kDa) over-sulfated exopolysaccharide (GYS15) prepared from a marine native exopolysaccharide excreted by a mesophilic marine bacterium from a deep-sea hydrothermal environment, and relates to the use of this low-molecular-weight over-sulfated exopolysaccharide for the prevention or inhibition of metastases formation.

7 Claims, 9 Drawing Sheets

(56) References Cited

OTHER PUBLICATIONS

Guezennec J et al: "Sulfation and depolymerization of a bacterial exopolysaccharide of hydrothermal origin", Carbohydrate Polymers, Applied Science Publishers, Ltd. Barking, GB, vol. 37, No. 1, Sep. 1, 1998, pp. 19-24.

Colliec Jouault AS et al: "Characterization, chemical modifications and in vitro anticoagulant properties of an exopolysaccharide produced by Alteromonas infernus", Biochimica et Biophysica Acta, vol. 1528, No. 2-3, Oct. 3, 2001, pp. 141-151.

Parish C R et al: "Identification of sulfated oligosaccharide-based inhibitors of tumor growth and metastasis using novel in vitro assays for angiogenesis and heparanase activity.", Cancer Research, vol. 59, No. 14, Jul. 15, 1999, pp. 3433-3441.

Yan Jing-Kun et al: "Sulfation and enhanced antioxidant capacity of an exopolysaccharide produced by the medicinal fungus Cordyceps sinensis.", Molecules, vol. 18, No. 1, 2012, pp. 167-177.

Ando et al., "Molecular Alterations Associated with Osteosarcoma Developement", Hindawi Publishing Corporation, Sarcoma, vol. 2012. pp. 1-12.

Odri et al., "Zoledronic acid inhibits pulmonary metastasis dissemination in a preclinical model of Ewing's sarcoma via inhibition of cell migration", BMC Cancer, Research Article, pp. 1-9, (2014).

Barkan et al., "Extracellular matrix: A gatekeeper in the transition from dormancy to metastatic growth", European Journal of Cancer, vol. 46, pp. 1181-1188, (2010).

Vismara et al., "Anti-metastatic Semi-synthetic Sulfated Maltotriose C—C Linked Dimers. Synthesis and Characterisation", Molecules, Article 17, pp. 9912-9930 (2012).

Feng et al., "Identification of Two Polysaccharides from *Prunella vulgaris* L. and Evaluation on Their Anti-Lung Adenocarcinoma Activity" Molecules, Article 15, pp. 5093-5103 (2010).

Bernd H. A. Rehm, Applied and Industrial Microbiology, Bacterial polymers: biosynthesis, modifications and applications, vol. 8, pp. 578-592, Aug. 2010.

Colliec-Jouault et al., "Heparin-like Entities from Marine Organisms" Handbook of Experimental Pharmacology, vol. 207, pp. 423-449, 2012.

Ruiz Velasco et al., Glycobiology, Effects of a sulfated exoploysaccharide produced by *Altermonas infernus* on bone biology, vol. 21 No. 6, pp. 781-195, 2011.

*Remington's Pharmaceutical Sciences*, E.W. Martin, 18th Ed., 1990, Mack Publishing Co.: Easton, PA. Cover Page and Table of Contents.

Zhang et al., Piperine inhibits proliferation of human osteosarcoma cells via G2/M phase arrest and meastasis by suppressing MMP-2/-9 expression, International Immunopharmacology, vol. 24, pp. 50-58, 2015.

Ma et al., "RNAi-mediated knockdown of relazin decreases in vitro proliferation and invasiveness of osteosarcoma MG-63 cells by inhibition of MMP-9" European Review of Medical and Pharmacological Sciences, vol. 17, pp. 1102-1109, 2013.

\* cited by examiner (A)

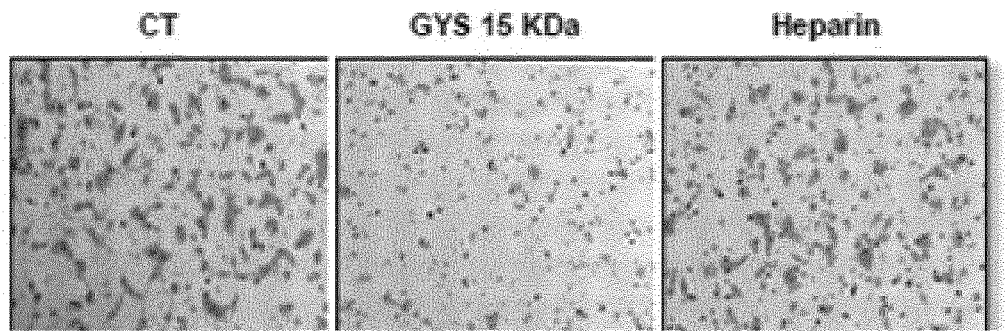
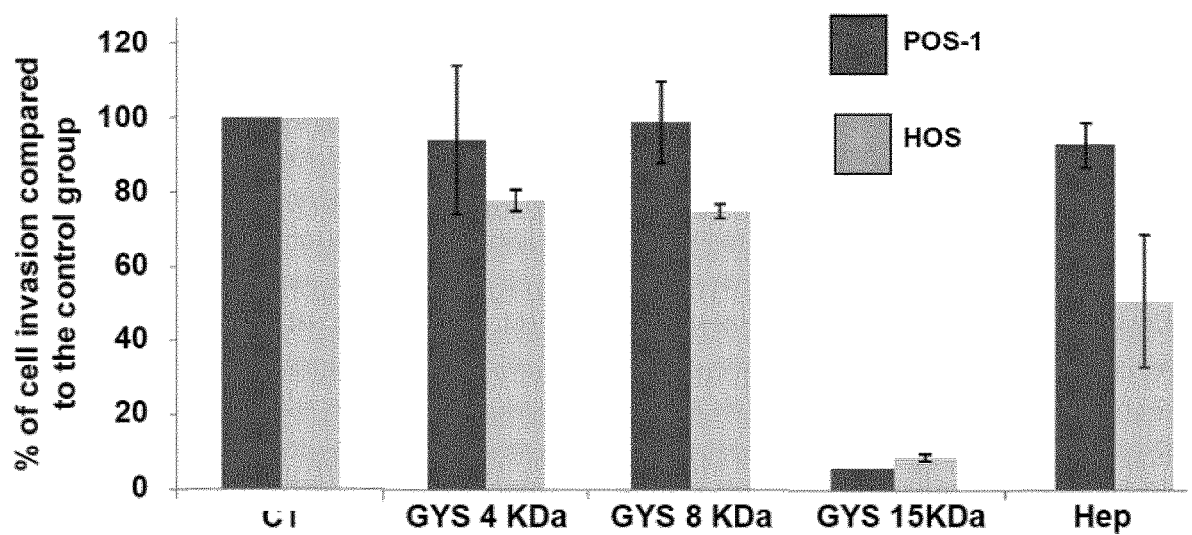
Figure 3(A)-(B)

(A)
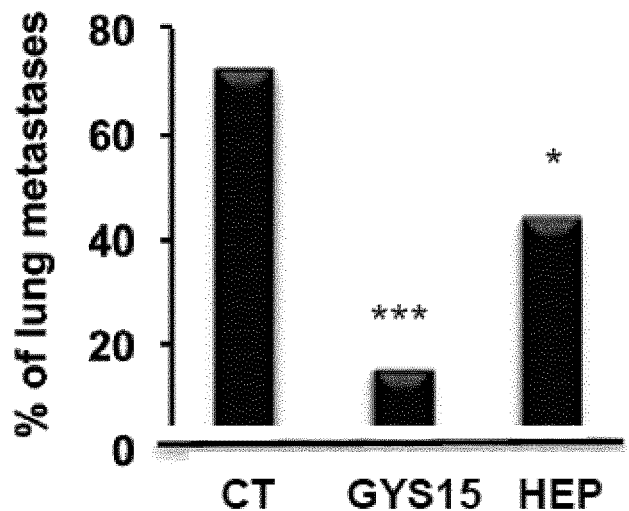
(B)
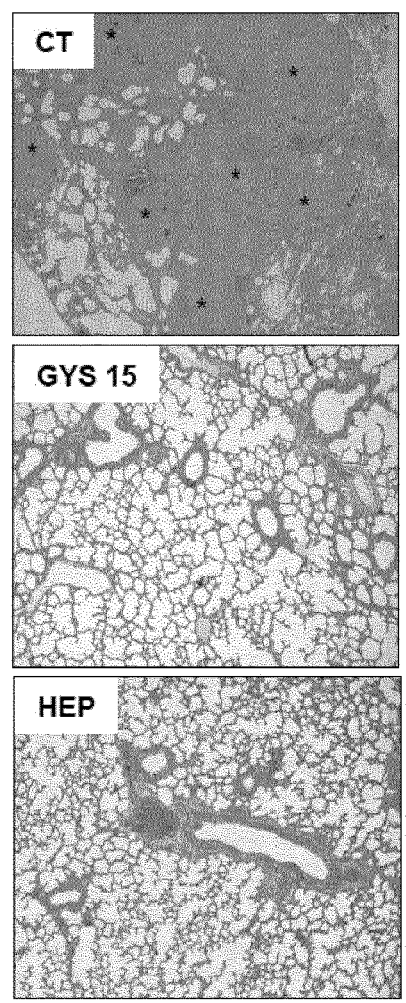
Figure 7(A)-(B)

ANTI-METASTATIC MARINE BACTERIAL EXOPOLYSACCHARIDE DERIVATIVE AND USES THEREOF

CROSS-REFERENCE TO RELATED PATENT APPLICATION

This present application is the U.S National Phase of PCT Application No. PCT/EP2016/073035 filed Sep. 28, 2016, which claims the benefit of priority of European Patent Application No. 15 187 107 filed on Sep. 28, 2015, the respective disclosures of which are incorporated herein by reference in their entireties.

BACKGROUND OF THE INVENTION

Osteosarcoma is the most frequent malignant primary bone tumor that occurs mainly in the young, with an incidence peak observed at 18 years of age. Despite recent improvements in chemotherapy and surgery, the problem of non-responsiveness to chemotherapy remains and this poor prognosis warrants new therapeutic strategies to improve the overall rate of survival. Osteosarcoma is characterized by a high potency to form metastases, which is the main cause of death (Ando et al., Sarcoma, 2012, 2012: 523432-523432; Odri et al., BMC Cancer, 2014, 14: 169-177).

Recent studies have described the molecular mechanisms of metastasis occurrence that can help to identify new therapeutic strategies (Barkan et al., Europ. J. Cancer, 2010, 46: 1181-1188). Carbohydrates, and especially heparin or heparan sulfate, are now considered as good candidates to treat cancers, in particular to treat cancer metastasis. However, their therapeutic use is limited because they both exhibit anticoagulant activity and therefore they can induce adverse bleeding complications. Another disadvantage of heparin and heparan sulfate is their animal origin, which can result in a high risk of unknown cross-species contamination (Stevenson et al., Research, 2007, 120: 5107-5111; Velasco et al., Drug Discov. Today, 2010, 15: 553-560). Consequently, the exploration of the therapeutic potential of heparin mimetics is now booming. Sulfated oligosaccharides are currently studied, such as a sulfated form of phosphomannopentaose and phosphomannotetraose named P1-88 (Ferro et al., Carbohydr. Res., 2001, 332: 183-189); sulfated form of maltohexose and sulfated maltotriose (Vismara et al., Molecules, 2012, 17: 9912-9930). Recently, two polysaccharides extracted from *Prunella vulgaris* L. were described for their anti-lung adenocarcinoma activity (Feng et al., Molecules, 2010, 15: 5096-5103).

In recent years, there has been a growing interest in the isolation and identification of new microbial polysaccharides that might have new applications in diverse industries. They compete with polysaccharides from other sources such as seaweeds, crustaceans, animals or plants. Interest in mass culture of microorganisms from the marine environment has increased considerably, representing an innovative approach to the biotechnological use of under-exploited resources. When they are sulfated, polysaccharides from different sources can share some biological properties with glycosaminoglycans (GAGs), and especially heparan sulfate or heparin, without exhibiting the same bleeding risks and with a low risk to be contaminated by a non-conventional transmissible agent such as prions or emerging viruses due to a large "species-barrier" (DeAngelis, Appl. Microbiol. Biotechnol., 2012, 94: 295-305).

Marine bacteria associated with deep-sea hydrothermal conditions have demonstrated their ability to produce, in an aerobic carbohydrate-based medium, unusual extracellular polymers. They present original structural features that can be modified to design bioactive compounds and improve their specificity (Rehm et al., Rev. Microbiol., 2010, 8: 578-592; Colliec-Jouault et al., Handbook of Exp. Pharmacol., 2012, 423-449). In particular, with the aim of promoting biological activities, chemical modifications (depolymerization and substitution reactions) of an exopolysaccharide (GY785 EPS) produced by a deep-sea hydrothermal bacterial named *Alteromonas infernus* have been undertaken. The structure of the native GY785 EPS has been described (Roger et al., Carbohydr. Res., 2004, 339: 2371-2380). A low molecular weight (LMW) over-sulfated exopolysaccharide (OS-EPS) of 24 kDa has been isolated after chemical modifications of this native GY785 EPS. This LMW derivative was found to be less efficient (10 fold) than heparin in clotting assays. In activated partial thromboplastin time, the same anticoagulant effect was obtained with a concentration of 10 µg/ml of 24 kDa OS-EPS and with a concentration of 1.5 µg/ml of heparin, respectively (Colliec-Jouault et al., Biochim. Biophys. Acta, 2001, 1528: 141-151).

The growth and differentiation of bone cells is controlled by various factors that can be modulated by heparan sulfates. The effects of the 24 kDa OS-EPS on bone biology have previously been studied. The effect of this highly sulfated LMW derivative (40% sulfate groups) has been compared to that of a non-oversulfated LWM EPS of 13 kDa (10% sulfate groups). The observed data have shown different levels of bone resorption regulation by GAGs or OS-EPS, most of them leading to pro-resorptive effects (Velasco et al., Glycobiology, 2011, 21: 781-795).

In spite of the progress made in promoting biological properties of exopolysaccharides, there still remains a need in the art to provide new therapeutic strategies to improve the overall rate of survival in metastatic cancer, in particular in metastatic osteosarcoma.

SUMMARY OF THE INVENTION

The present Inventors have shown that a low-molecular-weight over-sulfated polysaccharide obtained from a marine native exopolysaccharide (EPS) from the strain GY785 of the *Alteromonas* genus exhibits anti-metastatic properties. Indeed, in in vitro experiments, they first compared the activity of three low-molecular-weight over-sulfated polysaccharides with different molecular weights (4 kD (GYS4), 8 kDa (GYS8) and 15 kDa (GYS15)) on osteosarcoma cell lines (mouse POS-1 and human HOS cell lines), using heparin as a reference. Proliferation, migration, cell cycle analysis and expression in osteosarcoma cell lines of matrix metalloproteinases such as gelatinases MMP-2 and MMP-9 and their inhibitors TIMP-1 and TIMP-2 were studied. Then, GYS15, which showed the most interesting properties in vitro was evaluated in vivo on both primary malignant bone tumor growth (paratibial model) and formation of lung metastases in an osteosarcoma mouse model, again using heparin as a reference. The results obtained showed that GYS15 was very efficient at inhibiting the formation of lung metastases in vivo.

Accordingly, in a first aspect, the present invention relates to a 15 kDa over-sulfated exopolysaccharide for use in the prevention or inhibition of metastases formation in a subject, wherein said 15 kDa over-sulfated exopolysaccharide is obtained by a method comprising the following steps:
(a) a step consisting of free-radical depolymerization of a marine native exopolysaccharide (EPS) from the strain GY785 of the *Alteromonas* genus so as to obtain a depolymerized EPS having a molecular weight of 5,000 to 100,000 g/mol;

(b) a subsequent step consisting of sulfation of the depolymerized EPS to obtain an over-sulfated depolymerized EPS, comprising adding to the depolymerized EPS at least one sulfation agent in an amount sufficient to obtain a sulfated polysaccharide having a degree of sulfate-group substitution of between 10% and 45% by weight relative to the total weight of the over-sulfated depolymerized EPS; and (c) a subsequent step consisting of isolating the 15 kDa over-sulfated exopolysaccharide (GYS15) from the over-sulfated depolymerized EPS.

In certain embodiments, the step of isolating GYS15 from the over-sulfated depolymerized EPS is carried out by fractionation, in particular fractionation performed by size exclusion chromatography.

In certain preferred embodiments, the subject is a cancer patient. A cancer patient may be suffering from a cancer, or may have previously undergone therapy for cancer. When the cancer patient is suffering from a cancer, the cancer patient may be undergoing therapy for cancer.

The cancer of the patient may belong to the group consisting of carcinoma, lymphoma, blastoma, sarcoma, and leukemia. For example, the cancer may belong to the group consisting of bone cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma.

In certain embodiments, the cancer is osteocarcinoma.

In the same first aspect, the present invention provides a method for preventing or inhibiting the formation of metastases formation in a subject, comprising a step of administering to said subject a therapeutically effective amount of GYS15.

In certain preferred embodiments of the method of the invention, the subject is a cancer patient, as described above.

In another aspect, the present invention provides a pharmaceutical composition comprising a therapeutically effective amount of GYS15 and at least one pharmaceutically acceptable carrier or excipient for use in the prevention or inhibition of metastases formation in a subject.

In certain preferred embodiments of the method of the invention, the subject is a cancer patient, as described above.

These and other objects, advantages and features of the present invention will become apparent to those of ordinary skill in the art having read the following detailed description of the preferred embodiments.

Definitions

As used herein, the term "subject" refers to a human or another mammal (e.g., primate, dog, cat, goat, horse, pig, mouse, rat, rabbit, and the like), that can develop a cancer, but may or may not be suffering from the disease. Non-human subjects may be transgenic or otherwise modified animals. In many embodiments of the present invention, the subject is a human being. In such embodiments, the subject is often referred to as an "individual" or a "patient". These terms do not denote a particular age, and thus encompass newborns, children, teenagers, and adults. The term "patient" more specifically refers to an individual suffering from a disease. Thus, the term "cancer patient" refers to an individual suffering from a cancer. A cancer patient may or may not have been diagnosed with cancer. The term also includes individuals that have previously undergone therapy for cancer.

As used herein, the term "cancer" refers to or describes the physiological condition in mammals that is typically characterized by unregulated cell growth, lack of differentiation and ability to invade local tissues and metastasize. Cancer can develop in any tissue of any organ. Examples of cancers include, but are not limited to carcinoma, lymphoma, blastoma, sarcoma, and leukemia. More particularly, examples of such cancers include bone cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the pelvis, neoplasms of the central nervous system (CNS), neuroectodermal cancer, spinal axis tumors, glioma, meningioma, and pituitary adenoma.

The terms "aggressive" and "invasive" are used herein interchangeably. When used herein to characterize a cancer, they refer to the proclivity of a tumor for expanding beyond its boundaries into adjacent tissue. Invasive cancer can be contrasted with organ-confined cancer wherein the tumor is confined to a particular organ. The invasive property of a tumor is often accompanied by the elaboration of proteolytic enzymes, such as collagenases, that degrade matrix material and basement membrane material to enable the tumor to expand beyond the confines of the capsule, and beyond confines of the particular tissue in which that tumor is located.

The term "metastasis", as used herein, refers to the spread of tumor cells from one organ or tissue to another location. The term also refers to tumor tissue that forms in a new location as a result of metastasis. A "metastatic cancer" is a cancer that spreads from its original, or primary, location, and may also be referred to as a "secondary cancer" or "secondary tumor". Generally, metastatic tumors are named for the tissue of the primary tumor from which they originate. The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location.

As used herein, the term "inhibit" means to prevent something from happening, to delay occurrence of something happening, and/or to reduce the extent or likelihood of something happening. Thus, the terms "inhibiting metastasis", "inhibiting metastases" and "inhibiting the formation of metastases", which are used herein interchangeably, are intended to encompass preventing, delaying, and/or reducing the likelihood of occurrence of metastases as well as reducing the number, growth rate, size, etc. . . . of metastases.

The term "treatment" is used herein to characterize a method or process that is aimed at (1) delaying or preventing the onset of a disease or condition; (2) slowing down or stopping the progression, aggravation, or deterioration of the symptoms of the disease or condition; (3) bringing about amelioration of the symptoms of the disease or condition; or (4) curing the disease or condition. A treatment may be administered after initiation of the disease or condition, for a therapeutic action. Alternatively, a treatment may be administered prior to the onset of the disease or condition, for a prophylactic or preventive action. In this case, the term "prevention" is used.

A "pharmaceutical composition" is defined herein as comprising an effective amount of the low-molecular weight (LMW) over-sulfated exopolysaccharide derivative of the invention (i.e., OS-EPS 15 kDa or GYS15), and at least one pharmaceutically acceptable carrier or excipient.

As used herein, the term "therapeutically effective amount" refers to any amount of a compound, agent, or composition that is sufficient to fulfil its intended purpose(s), e.g., a desired biological or medicinal response in a cell, tissue, system or subject.

The term "pharmaceutically acceptable carrier or excipient" refers to a carrier medium which does not interfere with the effectiveness of the biological activity of the active ingredient(s) and which is not excessively toxic to the host at the concentration at which it is administered. The term includes solvents, dispersion media, coatings, antibacterial and antifungal agents, isotonic agents, and adsorption delaying agents, and the like. The use of such media and agents for pharmaceutically active substances is well known in the art (see for example "*Remington's Pharmaceutical Sciences*", E. W. Martin, 18$^{th}$ Ed., 1990, Mack Publishing Co.: Easton, Pa., which is incorporated herein by reference in its entirety).

The terms "approximately" and "about", as used herein in reference to a number, generally include numbers that fall within a range of 10% in either direction of the number (greater than or less than the number) unless otherwise stated or otherwise evident from the context (except where such number would exceed 100% of a possible value).

DETAILED DESCRIPTION OF CERTAIN PREFERRED EMBODIMENTS

As mentioned above, the present invention provides a low-molecular-weight over-sulfated exopolysaccharide derivative (GYS15) that exhibits anti-metastatic properties, and the use of this low molecular weight over-sulfated exopolysaccharide derivative for the prevention of metastases formation.

I—Low Molecular Weight Over-Sulfated Exopolysaccharide Derivatives

The invention relates to the use of GYS15, a low molecular weight (LMW) (15 kDa) over-sulfated exopolysaccharide (OS-EPS), which was prepared from a marine native exopolysaccharide (EPS) from the strain GY785 of the *Alteromonas* genus (*Alteromonas infernus*). The marine native EPS from the strain GY785 has previously been described (Guezennec et al., Carbohydr. Polym., 1998, 37: 19-24).

Processes for obtaining low-molecular-weight over-sulfated polysaccharide derivatives from the marine native exopolysaccharide according to the invention are fully described in the international application WO 2006/003290, and also by Colliec Jouault S. et al. in Biochim Biophys Acta 2001, 1528(2-3): p. 141-151, and by Guezenec J. et al. in Carbohydrate Polymers 1998, 37(1): p. 19-24.

In the practice of the present invention, GYS15 is prepared using a method comprising:

(a) a step consisting of free-radical depolymerization of a marine native exopolysaccharide (EPS) from the strain GY785 of the *Alteromonas* genus so as to obtain a depolymerized EPS having a molecular weight of 5,000 to 100,000 g/mol;

(b) a subsequent step consisting of sulfation of the depolymerized EPS to obtain an over-sulfated depolymerized EPS, comprising adding to the depolymerized EPS at least one sulfation agent in an amount sufficient to obtain a sulfated polysaccharide having a degree of sulfate-group substitution of between 10% and 45% by weight relative to the total weight of the over-sulfated depolymerized EPS; and (c) a subsequent step consisting of isolating the 15 kDa over-sulfated exopolysaccharide (GYS15) from the over-sulfated depolymerized EPS.

In certain embodiments, the depolymerized derivatives obtained after step (a) are lyophilized.

In other embodiments, step (b) of the process is followed by a dialysis step.

During the first depolymerization step, the native EPS can be used in a liquid form, i.e. as it is excreted by the bacteria into the culture medium. Preferably, the culture medium is centrifuged and only the supernatant containing the native EPS and that is free of bacterial debris is collected. The native EPS can be collected by any suitable technique known to those skilled in the art, such as for example membrane ultrafiltration, and can then optionally be lyophilized as is or in the form of an addition salt.

The step consisting of free-radical depolymerization of the native EPS is preferably carried out by addition of a solution of an oxidizing agent to a reaction mixture comprising the native EPS, preferably in the presence of a metal catalyst. The oxidizing agent is preferably chosen from peroxides, in particular hydrogen peroxide, and peracids, especially peracetic acid and 3-chloroperbenzoic acid. The addition is preferably carried out continuously and with stirring for a period of between 30 minutes and 10 hours. The reaction mixture is preferably maintained at a pH of between 6 and 8, for example by addition of a basifying agent such as sodium hydroxide, and at a temperature of between approximately 30° C. and 70° C. throughout the duration of the free-radical depolymerization reaction.

According to a specific embodiment of the present invention, in this step, the native EPS is present in the reaction mixture at a concentration of between about 2 mg/ml and about 10 mg/ml of reaction mixture.

In preferred embodiments, the oxidizing agent is a solution of hydrogen peroxide ($H_2O_2$) preferably having a concentration of between about 0.1% and about 0.5% by weight, preferably of the order of 0.1% to 0.2% by weight, and is added at a flow rate of V1/1000 to V1/10 ml/minute, preferably V1/50 and V1/500 ml/minute, and more preferably of the order of V1/100 ml/minute, wherein V1 is the volume of the reaction medium containing a marine exopolysaccharide (EPS) to which a solution of hydrogen peroxide is added.

The metal catalysts that can be used during the depolymerization step are preferably chosen from $Cu^{++}$, $Fe^{++}$ and $Cr^{+++}$ ions and the $Cr_2O_7^{2-}$ anion, as described in particular in patent application EP 0 221 977. According to a specific embodiment, the metal catalyst is present in the reaction mixture at a concentration of between about $10^{-3}$ M and about $10^{-1}$ M, and preferably at a concentration of between about 0.001 M and about 0.05 M.

The free-radical depolymerization process according to the invention and as described above makes it possible to obtain, in a single step and with a good yield, homogeneous, low-molecular-weight polysaccharide derivatives. In the context of the present invention, the term "homogeneous derivatives" is intended to mean derivatives which, when assessed using high performance size exclusion chromatography, exhibit a single main peak representing a predominant population of polysaccharide chains that are homogeneous with respect to size, characterized by a polydispersity index I (Mw/Mn)<5, where Mw is the weight-average molecular weight and Mn is the number-average molecular weight.

In certain embodiments, when the depolymerization reaction is over, the polysaccharide derivatives obtained are reduced using a reducing agent, so as to stabilize the chains, the reducing ends of which are very reactive, and in particular to avoid chain hydrolysis by the "peeling" reaction. The nature of the reducing agents that can be used to this effect is not essential. In particular, the reducing agent may be sodium borohydride.

The metal catalyst used in the depolymerization step can be eliminated at the end of the depolymerization reaction, (or at the end of the reduction reaction if a reduction step is carried out) using any suitable method, for example by ion exchange chromatography, preferably a weak cation exchange resin passivated beforehand, or by treatment with EDTA (ethylenediaminetetraacetic acid).

The polysaccharide derivatives resulting from the depolymerization and/or from the reduction can, if necessary, be recovered by any suitable technique well known to those skilled in the art, such as, for example, by membrane ultrafiltration or dialysis. Then, they are lyophilized and fractionated by size exclusion chromatography to increase their purity required to improve the subsequent sulfation step. Finally, the purified polysaccharide derivatives are conditioned in salt form by addition of a weak or strong base that may be chosen, for example, from pyridine, triethylamine, tributylamine, tetrabutylammonium hydroxide and sodium hydroxide. This lyophilized salt may be prepared, for example, by elution of an aqueous solution of the polysaccharide derivatives at a concentration of between 1 and 8 mg/ml on an ion exchange resin column such as, for example, those sold under the name DOWEX® by the company Dow Chemical. The eluate is collected as long as the pH remains acid, for example less than 5, then the pH is subsequently adjusted to approximately 6.5 with the desired base as defined above. The polysaccharide derivatives in the form of a salt are then ultrafiltered and lyophilized.

The lyophilized polysaccharide derivatives, possibly in the form of an addition salt, are preferably dissolved in an anhydrous solvent at the beginning of the sulfation step. The solvent is preferably chosen from dimethylformamide (DMF), dimethyl sulfoxide (DMSO) formamide, and mixtures thereof. The amount of polysaccharide derivatives present in the anhydrous solvent may be between approximately 1 and 10 mg/ml, preferably between about 1 mg/ml and about 5 mg/ml, and even more preferably this amount is about 2.5 mg/ml. The dissolution of the EPS in the anhydrous solvent is preferably carried out, with stirring, at ambient temperature for about 1 hour to about 2 hours and then at a temperature of between 40° C. and 50° C., preferably at a temperature of about 45° C. for about 2 hours under argon or azote with molecular sieve.

The one or more chemical sulfation agents used during the sulfation step can be added to the depolymerized and/or reduced EPSs that are in lyophilized form or in the form of a solution.

The sulfation agents are preferably chosen from complexes of pyridine sulfate (free or coupled to a polymer), of dimethylformamide sulfate, triethylamine sulfate and of trimethylamine sulfate. The one or more chemical sulfation agents are added to the solution of polysaccharide derivatives in a weight amount preferably representing from about 4 to about 6 times, and even more preferably about 5 times, the mass of polysaccharide derivatives in solution. The chemical sulfation reaction is then preferably carried out with stirring for a period of between 2 and 24 hours depending on the desired degree of sulfation. When the desired degree of sulfation is reached, the sulfation reaction is stopped after cooling of the reaction medium:

either by precipitation in the presence of sodium-chloride-saturated acetone or of methanol, and then dissolution of the precipitate in water;

or, preferably, by addition of water in a proportion preferably equal to 1/10 of the reaction volume and adjustment of the pH of the reaction medium to 9 with a basifying agent such as, for example, sodium hydroxide (3 M).

According to certain embodiments, the solution of sulfated polysaccharide derivatives is preferably dialyzed in order to remove the various salts, and then lyophilized. The final product (i.e., GYS15), typically with an accurate molecular weight and a low polydispersity index, is obtained by isolation from the low-molecular weight depolymerized EPS obtained. Isolation may be performed by any suitable method known in the art. Preferably, isolation is carried out by fractionation performed by size exclusion chromatography.

GYS15 according to the present invention has a low polydispersity index of less than 5, preferably of 1.5 to 4, more preferably of less than 2. The polydispersity index (PDI) according to the invention is a measure of the distribution of molecular mass of the derivatives. The PDI calculated is the weight average molecular weight divided by the number average molecular weight. PDI is typically measured by size-exclusion chromatography.

GYS15 according to the invention has a degree of sulfate-group substitution of between 10% and 45% by weight relative to the total weight of the sulfated polysaccharide derivative. In certain embodiments, the degree of sulfate-group substitution is of between 10% and 40%, of between 20% and 45% or of between 20% and 40%.

II—Uses of the Low Molecular Weight OS-EPS Derivative

1—Therapeutic Applications

A. Indications

The GYS derivative of the present invention may be used in the prevention or inhibition of the formation of metastases in a subject.

Methods of prevention of the present invention may be accomplished using GYS15 or a pharmaceutical composition thereof. These methods generally comprise administration of an effective amount of GYS15 (as defined above), or a pharmaceutical composition thereof, to a subject in need thereof. Administration may be performed using any of the methods known to one skilled in the art. In particular, GYS15, or a composition thereof, may be administered by any of various routes including, but not limited to, aerosol, parenteral, oral or topical route.

Generally, the subject is a human cancer patient. The cancer patient may be suffering from a cancer or having previously undergone therapy of cancer.

In the practice of the present invention, the cancer may be any cancer developed in any tissue of any organ. Thus, the cancer may be a carcinoma, lymphoma, blastoma, sarcoma, and leukemia. Examples of cancers include, but are not limited to, bone cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the pelvis, neoplasms of the central nervous system (CNS), neuroectodermal cancer, spinal axis tumors, glioma, meningioma, and pituitary adenoma. In certain embodiments, the cancer is osteocarcinoma.

In general, GYS15, or a composition thereof, will be administered in an effective amount, i.e., an amount that is sufficient to fulfill its intended purpose. The exact amount of GYS15, or pharmaceutical composition, to be administered will vary from subject to subject, depending on the age, sex, weight and general health condition of the subject to be treated, the desired biological or medical response and the like. In certain embodiments, an effective amount is one that prevents, delays and/or reduces the likelihood of occurrence of metastases formation and/or one that reduces the number, growth rate, size, etc. . . . of metastases if metastases are already present in the subject. The effects of a treatment according to the invention may be monitored using any of the diagnostic assays, tests and procedures known in the art.

In certain embodiments, GYS15, or a composition thereof, is administered alone according to a method of prevention according to the present invention. In other embodiments, GYS15, or a composition thereof, is administered in combination with at least one additional therapeutic agent or therapeutic procedure. GYS15, or a composition thereof, may be administered prior to administration of the therapeutic agent or therapeutic procedure, concurrently with the therapeutic agent or procedure, and/or following administration of the therapeutic agent or procedure.

Therapeutic agents that may be administered in combination with GYS15, or a composition thereof, may be selected among a large variety of biologically active compounds that are known to have a beneficial effect in the treatment of cancer or to a patient in general (e.g. anti-cancer agents, anti-inflammatory agents, immunomodulatory agents, analgesics, antimicrobial agents, antibacterial agents, antibiotics, antioxidants, antiseptic agents, and combinations thereof). Therapeutic procedures that may be performed in combination with administration of GYS15, or a composition thereof, include, but are not limited to, surgery, radiotherapy, and the like.

Anti-cancer agents that may be administered in combination with GYS15, or a composition thereof, include drugs conventionally classified in one of the following group: alkylating agents, purine antagonists, pyrimidine antagonists, plant alkaloids, intercalating antibiotics, aromatase inhibitors, anti-metabolites, mitotic inhibitors, growth factor inhibitors, cell cycle inhibitors, enzymes, topoisomerase inhibitors, biological response modifiers, anti-hormones and anti-androgens. Examples of such anti-cancer agents include, but are not limited to, BCNU, cisplatin, gemcitabine, hydroxyurea, paclitaxel, temozolomide, topotecan, fluorouracil, vincristine, vinblastine, procarbazine, decarbazine, altretamine, methotrexate, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomycin, tamoxifen, flutamide, leuprolide, goserelin, aminogluthimide, anastrozole, amsacrine, asparaginase, mitoxantrone, mitotane and amifostine.

Other examples of such anti-cancer agents include therapeutic antibodies used in the treatment of cancer, including, but are not limited to, anti-CD52 antibodies such as alemtuzumab (CAMPATH), which is used in the treatment of chronic lymphocytic leukemia; anti-VEGF antibodies including bevacizumab (AVASTIN™) which is used in the treatment of colorectal cancer and breast cancer; anti-CD33 antibodies, including gemtuzumab ozogamicin (MYLOTARG™) which is used in the treatment of acute myeloid leukemia; anti-CD20 antibodies including ibritumomab (ZEVALIN™) which is used in the treatment of lymphoma, rituximab (RITUXAN™) which is used in the treatment of Hodgkin lymphoma, tositumomab (BEXXAR) which is used in the treatment of Hodgkin lymphoma and ofatumumab (ARZERRA™) which is used in the treatment of chronic lymphocytic leukemia; anti-EGFR antibodies such as cetuximab (ERBITUX™) which is used in the treatment of colorectal cancer, head and neck cancer, and squamous cell carcinoma, and panitumumab (VECTIBEX™) which is used in the treatment of colorectal cancer; anti-Her2 antibodies, including trastuzumab (HERCEPTIN™) which is used in the treatment of breast cancer and stomach cancer; anti-CTLA4 antibodies including Ipilimumab (YERVOY™) which is used in the treatment of melanoma; adnectins; and domain antibodies. Active fragments and fusions of these antibodies will also find use herein.

B. Administration

GYS15 (optionally after formulation with one or more appropriate pharmaceutically acceptable carriers or excipients), in a desired dosage can be administered to a subject in need thereof by any suitable route. Various delivery systems are known and can be used to administer the GYS derivative of the present invention, including tablets, capsules, injectable solutions, encapsulation in liposomes, microparticles, microcapsules, etc. Methods of administration include, but are not limited to, dermal, intradermal, intramuscular, intraperitoneal, intralesional, intravenous, subcutaneous, intranasal, pulmonary, epidural, ocular, and oral routes. GYS15, or a composition thereof, may be administered by any convenient or other appropriate route, for example, by infusion or bolus injection, by adsorption through epithelial or mucocutaneous linings (e.g., oral, mucosa, rectal and intestinal mucosa, etc). Administration can be systemic or local. Parenteral administration may be directed to a given tissue of the patient, such as by catheterization. As will be appreciated by those of ordinary skill in the art, in embodiments where GYS15 is administered along with an additional therapeutic agent, GYS15 and the therapeutic agent may be administered by the same route (e.g., orally) or by different routes (e.g., orally and intravenously).

C. Dosage

Administration of GYS15 (or a composition thereof) according to the present invention will be in a dosage such that the amount delivered is effective for the intended purpose. The route of administration, formulation and dosage administered will depend upon the therapeutic effect desired, the severity of the disorder being treated, the presence of any infection, the age, sex, weight and general health condition of the patient as well as upon the potency, bioavailability and in vivo half-life of the GYS15, the use (or not) of concomitant therapies, and other clinical factors. These factors are readily determinable by the attending physician in the course of the therapy. Alternatively or additionally, the dosage to be administered can be determined from studies using animal models. Adjusting the dose to achieve maximal efficacy based on these or other methods is well known in the art and is within the capabilities of trained physicians. As studies are conducted using GYS15, further information will emerge regarding the appropriate dosage levels and duration of treatment.

A treatment according to the present invention may consist of a single dose or multiple doses. Thus, administration of GYS15, or a composition thereof, may be constant for a certain period of time or periodic and at specific intervals, e.g., hourly, daily, weekly (or at some other multiple day interval); monthly, yearly (e.g., in a time release form). Alternatively, the delivery may occur at multiple times during a given time period, e.g., two or more times per week, two or more times per month, and the like. The delivery may be continuous delivery for a period of time, e.g., intravenous delivery.

III—Pharmaceutical Compositions

As mentioned above, the GYS derivative of the invention may be administered per se or as a pharmaceutical composition. Accordingly, the present invention provides pharmaceutical compositions comprising an effective amount of GYS15 and at least one pharmaceutically acceptable carrier or excipient. In some embodiments, the composition further comprises one or more additional biologically active agents.

GYS15, or pharmaceutical compositions thereof, may be administered in any amount and using any route of administration effective for achieving the desired prophylactic therapeutic effect. The optimal pharmaceutical formulation can be varied depending upon the route of administration and desired dosage. Such formulations may influence the physical state, stability, rate of in vivo release, and rate of in vivo clearance of the administered active ingredient.

The pharmaceutical compositions of the present invention may be formulated in dosage unit form for ease of administration and uniformity of dosage. The expression "unit dosage form", as used herein, refers to a physically discrete unit of for the patient to be treated. It will be understood, however, that the total daily dosage of the compositions will be decided by the attending physician within the scope of sound medical judgement.

A. Formulation

Injectable preparations, for example, sterile injectable aqueous or oleaginous suspensions may be formulated according to the known art using suitable dispersing or wetting agents, and suspending agents. The sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose any bland fixed oil can be employed including synthetic mono- or di-glycerides. Fatty acids such as oleic acid may also be used in the preparation of injectable formulations. Sterile liquid carriers are useful in sterile liquid form compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered by, for example, intravenous, intramuscular, intraperitoneal or subcutaneous injection. Injection may be via single push or by gradual infusion. Where necessary or desired, the composition may include a local anesthetic to ease pain at the site of injection.

In order to prolong the effect of an active ingredient, it is often desirable to slow the absorption of the ingredient from subcutaneous or intramuscular injection. Delaying absorption of a parenterally administered active ingredient may be accomplished by dissolving or suspending the ingredient in an oil vehicle. Injectable depot forms are made by forming micro-encapsulated matrices of the active ingredient in biodegradable polymers such as polylactide-polyglycolide. Depending upon the ratio of active ingredient to polymer and the nature of the particular polymer employed, the rate of ingredient release can be controlled. Examples of other biodegradable polymers include poly(orthoesters) and poly (anhydrides). Depot injectable formulations can also be prepared by entrapping the active ingredient in liposomes or microemulsions which are compatible with body tissues.

Liquid dosage forms for oral administration include, but are not limited to, pharmaceutically acceptable emulsions, microemulsions, solutions, suspensions, syrups, elixirs, and pressurized compositions. In addition to the GYS derivative, the liquid dosage form may contain inert diluents commonly used in the art such as, for example, water or other solvent, solubilising agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols, and fatty acid esters of sorbitan and mixtures thereof. Besides inert diluents, the oral compositions can also include adjuvants such as wetting agents, suspending agents, preservatives, sweetening, flavouring, and perfuming agents, thickening agents, colors, viscosity regulators, stabilizes or osmo-regulators. Examples of suitable liquid carriers for oral administration include water (potentially containing additives as above, e.g., cellulose derivatives, such as sodium carboxymethyl cellulose solution), alcohols (including monohydric alcohols and polyhydric alcohols such as glycols) and their derivatives, and oils (e.g., fractionated coconut oil and *arachis* oil). For pressurized compositions, the liquid carrier can be halogenated hydrocarbon or other pharmaceutically acceptable propellant.

Solid dosage forms for oral administration include, for example, capsules, tablets, pills, powders, and granules. In such solid dosage forms, the inventive GYS derivative may be mixed with at least one inert, pharmaceutically acceptable excipient or carrier such as sodium citrate or dicalcium phosphate and one or more of: (a) fillers or extenders such as starches, lactose, sucrose, glucose, mannital, and silicic acid; (b) binders such as, for example, carboxymethylcellulose, alginates, gelatine, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulfate, and mixtures thereof. Other excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents.

Solid compositions of a similar type may also be employed as fillers in soft and hard-filled gelatine capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition such that they release the active ingredient(s) only, or preferably, in a certain part of the intestinal tract, optionally, in a delaying manner. Examples of embedding compositions which can be used include polymeric substances and waxes.

In certain embodiments, it may be desirable to administer an inventive composition locally to a specific area. This may be achieved, for example, and not by way of limitation, by local infusion during surgery, topical application, by injection, by means of a catheter, by means of suppository, or by means of a skin patch or stent or other implant.

For topical administration, the composition is preferably formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurat (5%) in water, or sodium lauryl sulfate (5%) in water. Other materials such as antioxidants, humectants, viscosity stabilizers, and similar agents may be added as necessary.

In addition, in certain instances, it is expected that the inventive compositions may be disposed within transdermal devices placed upon, in, or under the skin. Such devices include patches, implants, and injections which release the active ingredient by either passive or active release mechanisms. Transdermal administrations include all administration across the surface of the body and the inner linings of bodily passage including epithelial and mucosal tissues. Such administrations may be carried out using the present compositions in lotions, creams, foams, patches, suspensions, solutions, and suppositories (rectal and vaginal).

Transdermal administration may be accomplished through the use of a transdermal patch containing an active ingredient (i.e., the GYS derivative) and a carrier that is non-toxic to the skin, and allows the delivery of the ingredient for systemic absorption into the bloodstream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may be suitable. A variety of occlusive devices may be used to release the active ingredient into the bloodstream such as a semi-permeable membrane covering a reservoir containing the active ingredient with or without a carrier, or a matrix containing the active ingredient.

Suppository formulations may be made from traditional materials, including cocoa butter, with or without the addition of waxes to alter the suppository's melting point, and glycerine. Water soluble suppository bases, such as polyethylene glycols of various molecular weights, may also be used.

Materials and methods for producing various formulations are known in the art and may be adapted for practicing the subject invention. Suitable formulations for the delivery of antibodies can be found, for example, in "*Remington's Pharmaceutical Sciences*", E. W. Martin, 18$^{th}$ Ed., 1990, Mack Publishing Co.: Easton, Pa.

B. Additional Biologically Active Agents

In certain embodiments, GYS15 is the only active ingredient in a pharmaceutical composition of the present invention. In other embodiments, the pharmaceutical composition further comprises one or more biologically active agents. Examples of suitable biologically active agents include, but are not limited to, anti-cancer agents, anti-inflammatory agents, immunomodulatory agents, analgesics, antimicrobial agents, antibacterial agents, antibiotics, antioxidants, antiseptic agents, and combinations thereof. Examples of specific anti-cancer agents, including anti-cancer antibodies have been listed above.

In such pharmaceutical compositions, the GYS derivative and the at least one additional therapeutic agent may be combined in one or more preparations for simultaneous, separate or sequential administration of the GYS derivative and therapeutic agent(s). More specifically, an inventive composition may be formulated in such a way that the GYS derivative and therapeutic agent(s) can be administered together or independently from each other. For example, the GYS derivative and a therapeutic agent can be formulated together in a single composition. Alternatively, they may be maintained (e.g., in different compositions and/or containers) and administered separately.

C. Pharmaceutical Packs of Kits

In another aspect, the present invention provides a pharmaceutical pack or kit comprising one or more containers (e.g., vials, ampoules, test tubes, flasks or bottles) containing one or more ingredients of an inventive pharmaceutical composition, allowing administration of the GYS derivative of the present invention.

Different ingredients of a pharmaceutical pack or kit may be supplied in a solid (e.g., lyophilized) or liquid form. Each ingredient will generally be suitable as aliquoted in its respective container or provided in a concentrated form. Packs or kits according to the invention may include media for the reconstitution of lyophilized ingredients. Individual containers of the kits will preferably be maintained in close confinement for commercial sale.

In certain embodiments, a pack or kit includes one or more additional therapeutic agent(s). Optionally associated with the container(s) can be a notice or package insert in the form prescribed by a governmental agency regulating the manufacture, use or sale of pharmaceutical or biological products, which notice reflects approval by the agency of manufacture, use or sale for human administration. The notice of package insert may contain instructions for use of a pharmaceutical composition according to methods of treatment disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

Further aspects and advantages of this invention will be disclosed in the following figures and examples, which should be regarded as illustrative and not limiting the scope of this application.

BRIEF DESCRIPTION OF THE FIGURES

FIG. 3: Invasion of osteosarcoma cell lines, the mouse POS-1 cell line and the human HOS cell line, in the presence of LMW OS-EPS derivatives with different molecular weights: 25 µg/mL OS-EPS 15 kDa (GYS15), 50 µg/mL OS-EPS 8 kDa (GYS8), 50 µg/mL OS-EPS 4 kDa (GYS4), 50 µg/mL heparin (Hep) and control (CT). (A) Microscopic pictures of invasive HOS cells treated or not with GYS15 or heparin. (B) Cells migrating through the Boyden's chambers were counted in 5 microscopic fields using Image J software. *$p<0.05$; ***$p<0.01$.

EXAMPLES

Figure 1A:
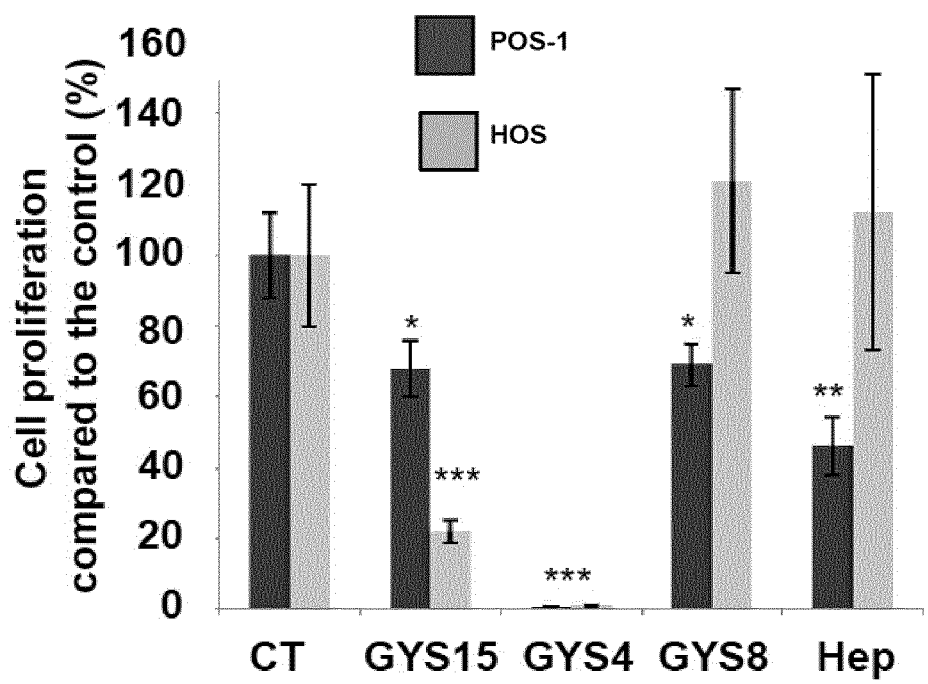
FIG. 1: Comparison of the effects of LMW OS-EPS derivatives with different molecular weights on two osteosarcoma cell lines, the mouse POS-1 cell line and the human HOS cell line. (A) Proliferation of both cell lines after 7 days of treatment. (B) Kinetics of biological activity of increasing doses of GYS15 on HOS cells proliferation. Proliferation assays were performed by cell counting with Trypan Blue to compare the cell proliferation rate between groups. OS-EPS 15 kDa (GYS15), OS-EPS 8 kDa (GYS8), OS-EPS 4 kDa (GYS4), heparin (Hep) and control (CT). *$p<0.05$, $p<0.01$, *$p<0.001$.

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Materials and Methods

General

The bacterial GY785 exopolysaccharide (EPS) was produced, purified and characterized as previously described (Guezennec et al., Carbohydr. Polym., 1998, 37: 19-24). The preparation, purification and characterization of low molecular weight (LMW) over-sulfated (OS) EPS derivatives were performed as previously reported (Ruiz Velasco et al., Glycobiology, 2011, 21: 781-795; WO 2006/003290). Briefly, native high molecular weight (HMW) GY785 EPS was depolymerized first using a free-radical depolymerisation process to obtain LMW derivatives with different molecular weights. LMW GY785 EPS derivatives were then sulfated in dimethylformamide (DMF) using pyridine sulfate as sulfating agent leading to LMW OS-EPS derivatives. Molecular weights (Mws) before and after sulfation were determined by HPSEC-MALS and sulfur content (wt % S) by HPAEC chromatography. ATR-FTIR and NMR spectroscopy were used to assess the efficiency of sulfation reaction. Heparin sodium salt from porcine intestinal mucosa H4784 was purchased from Sigma.

Proliferation Assays

Cells from the POS-1 cell line were cultured in RPMI (Roswell Park Memorial Institute, Biowhittaker) medium with 10% fetal bovine serum (FBS, Hyclone, France). Cells from the KHOS/NP cell line (HOS, (ATCC, USA)) were cultured in DMEM (Dulbecco's Modified Eagle Medium, Biowhittaker) with 5% FBS. The cells, initially seeded at the concentration of $50 \times 10^3$ cells/cm$^2$ were incubated at 37° C. with humidity saturated controlled atmosphere and 5% CO$_2$. At confluence, the cells were detached using trypsine-EDTA (Biowhittaker, Trypsine: 0.5 g/L; EDTA (Ethylene Diamine Tetraacetic Acid): 0.2 g/L). Trypsine was neutralized by adding FBS-containing medium and cells were collected after centrifugation at 400 g. Cells from the POS-1 and HOS cell lines were seeded in triplicate at 2000 cells per well in a 24-well plate with 500 µL of medium and treated in the presence of GYS4 or GYS8 or GYS15 (25, 50 or 100 µg/ml) or with PBS (control). Proliferation assays were performed by manually counting live cells using a Malassez cell with Trypan Blue to compare the cell proliferation rate between groups.

Migration Assays

Cells seeded ($4 \times 10^5$) in 6-well plates in duplicate were treated with mitomycin C (Sigma—4 µg/ml for 1 hour) to block cell proliferation and the migration of cells was evaluated in the presence of GYS4 or GYS8 or GYS15 (25 or 50 µg/ml) or with PBS (control). At confluence, cells were carefully scratched to create a gap. Images of the gap were acquired using an Olympus DP12-2 camera (Olympus Corporation, Tokyo, Japan) immediately after the beginning of the incubation and 24 hours, 48 hours and 72 hours after the beginning of incubation.

Invasion Assays

Invasion of cultured cells (POS-1 and HOS) was analyzed using Boyden's chambers (8 µm pores, Becton Dickinson Labware) covered with a polyethylene terephthalate membrane with MATRIGEL® coating (2 µg/100 µL/well in cold PBS) in 24-wells plate (MULTIWELL™ 24, FALCON®). The LMW OS-EPS 4 or 8 or 15 kDa derivatives (25, 50, 100 or 200 µg/ml) were added on the Matrigel 30 minutes before cell seeding. Cells previously treated with mitomycin C (Sigma—4 µg/ml for 1 hour) were seeded in the upper compartment of 500 µl cups in 1% FBS medium ($2 \times 10^4$ POS-1 cells or $3 \times 10^4$ HOS cells) and left for a 24 hour incubation at 37° C. in 5% $CO_2$ humidified atmosphere. The bottom wells in the system were filled with 10% FBS medium (700 µl) as a chemoattractant. At the end of the 24 hour-period, non-invasive cells were removed with cotton swabs and invading cells present on the inferior surface of the membrane were fixed with 3% PFA (Paraformaldehyde) and stained with methylene blue. After drying, the invasive cells were counted in 5 microscopic fields using Image J software (Leica). All the experiments were performed 3 times in duplicate. Invasion is expressed by mean number of cells/field.

Cell Cycle Analysis

Cells were incubated for 24 hours, 48 hours or 72 hours in medium containing or not LMW OS-EPS derivatives. After the incubation period, trypsinized cells were incubated in phosphate-buffered saline containing 0.12% Triton X-100, 0.12 mmol/L ethylenediamine tetraacetic acid, and 100 µg/mL DNase-free RNase A (Sigma). Then, 50 µg/mL propidium iodide were added, and the cells were incubated for 20 minutes at 4° C. in the dark. Cell cycle distribution was studied by flow cytometry (Cytomics FC500; Beckman Coulter, Roissy, France) based on 2N and 4N DNA content and analyzed by using DNA Cell Cycle Analysis Software (Phoenix Flow Systems, San Diego, Calif.) (Kapp et al., Expert Opin. Ther. Pat. 2013, 23: 1273-1295).

Matrix Metalloproteinase Expression

Cells were seeded ($5 \times 10^5$) in petri dishes (diameter of 60 mm) in 3 ml of medium with FBS. At confluence, cells were treated 1 hour, 3 hours, 6 hours, 8 hours or 24 hours with the LMW OS-EPS 15 KDa derivative, GYS15, or heparin at 50 µg/ml or with PBS (control). Matrix Metalloproteinase (MMP) and Tissue Inhibitors of Metalloproteinase (TIMP) expression was determined by quantitative-polymerase chain reaction (qPCR). RNA was extracted using NucleoSpin RNAII (Macherey Nagel, Duren, Germany) and used for first strand cDNA synthesis using ThermoScript realtime polymerase chain reaction (RT-PCR) System (Invitrogen, Carlsbad, Calif., USA). Quantitative PCR (qPCR) was performed with a Chromo4 instrument (Biorad, Richmond, Calif., USA) using SYBR Green Supermix reagents (Biorad).

Animal Ethics

All procedures involving animals were conducted in accordance with the Directive 2010/63/EU of the European Parliament and the Council of Sep. 22, 2010 on the protection of animals used for scientific purposes. The protocols presented in this study were approved by the French ethics committee (CEEA PdL. 06) with the protocol number 2010.34 and under the supervision of the authorized investigators. Four-week-old male NMRI-Nude mice [n=6] and four-week-old male C3H/HeN mice [n=7] from Elevages Janvier (Le Genest Saint Isle, France) were maintained under pathogen-free conditions at the Experimental Therapy Unit (Faculty of Medicine, Nantes, France) in accordance with the institutional guidelines of the French Ethics Committee (CEEA Pays de la Loire—06).

Osteosarcoma Mouse Model

Four-week-old male NMRI-Nude mice [n=6 per group] were anesthetized by inhalation of an isoflurane/air mixture (1.5%, 1 L/min) before receiving an intramuscular injection of $2 \times 10^6$ HOS cells in the paratibial area (in 50 µl of PBS buffer) (Moriceau et al., Cancer, 2012, 118: 750-760). Similarly, $1.5 \times 10^6$ POS-1 cells [n=6 per group] were inoculated in four-week-old female C57BL/6 mice (Segaliny et al., "Interleukin-34 promotes tumor progression and metastatic process in osteosarcoma through induction of angiogenesis and macrophage recruitment", Int. J. Cancer, 2015, in press). Tumors appeared at the injection site 8 days later. The tumor volume (V) was calculated from the measurement of two perpendicular diameters using a caliper, according to the following formula: $V=0.5 \times L \times (S)^2$, wherein L and S are, respectively, the largest and smallest perpendicular tumor diameters. A curative protocol was performed, when the tumor volume reached 100 $mm^3$, mice were treated with PBS (control) or with the LMW OS-EPS derivative. The polysaccharides diluted in PBS buffer (50 µL) were injected subcutaneously each day at 2 mg/kg or 6 mg/kg and the tumor growth was measured from Day 5 to Day 35. This mouse model (paratibial model) was preferred to the model using the injection of tumor cells directly into the tibia (intratibial model) because bone lesions were very similar at the end of the experiment in the two models and because the results are more reproducible in the former model (i.e., the paratibial model). In addition, the paratibial model mimics more closely the bone lesions observed in human.

Lung Metastasis Mouse Model

In order to study the effect of LMW OS-EPS derivatives on the metastatic ability of osteosarcoma, $1.5 \times 10^5$ POS-1 cells were injected using the technique of retro-orbital injection of the venous sinus (Ory et al., Cancer, 2005, 104: 2522-2529). Mice were anesthetized by inhalation of a combination isoflurane/air (1.5%, 1 L/min) and they received buprenorphine after the tumor cell injection (0.05 mg/kg; TEMGESIC®, Schering-Plough). A preventive protocol was established with four-week-old male C3H/HeN mice [n=7 per group] divided in 3 groups of treatment: PBS, heparin and GYS15. A first subcutaneous injection (12 mg/kg of GYS15 or heparin in 50 µl of PBS) was performed 30 minutes before the POS-1 cell injection. Then, 4 subcutaneous injections were performed daily at 6 mg/kg for GYS15 or heparin. Mice were euthanized when mice showed signs of lung metastases development (respiratory distress, weakness, weight loss, dorsal kyphosis). Lungs were collected for histological analysis and macroscopic analysis: the lungs were categorized according to the size (big or small) of the metastases.

Statistical Analysis

All in vitro experiments were realized 3 times. The numbers of cells per field mean counts were compared by a nonparametrical Wilcoxon test. Mean tumor volumes were compared using the Kruskal-Wallis test. The size of lung metastases categorical variable was analyzed by Fisher's exact test. The difference was considered significant at $p<0.05$.

Results

In Vitro Effect of LMW OS-EPS on Osteosarcoma Cell Lines

Figure 1B:
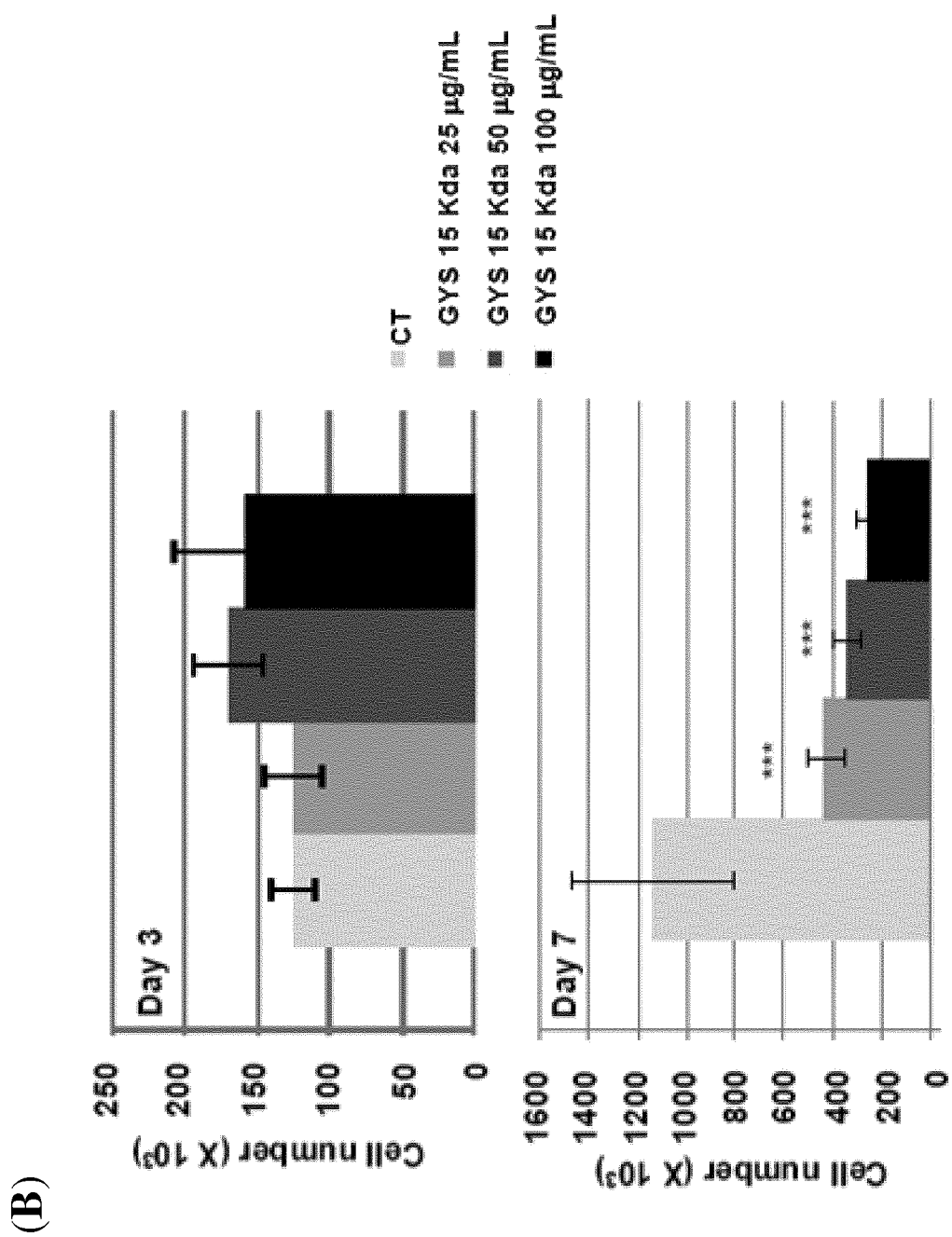

Cell Proliferation and Cell Viability. Compared to the controls, only GYS4 and GYS15 significantly inhibited both mouse POS-1 and human HOS cell proliferation. The most potent LMW OS-EPS derivative to inhibit the proliferation of osteosarcoma cell lines was found to be GYS4 (FIG. 1A). GYS8 was equally potent as heparin to inhibit POS-1 cell proliferation but they did not act as efficiently on cells of the HOS cell line (FIG. 1A). While 3 days of treatment with GYS15 did not result in any significant effect on HOS cell proliferation, 25 µg/mL of GYS15 markedly decreased the HOS cell proliferation after 7 days of treatment (FIG. 1B). In terms of cell viability, no significant difference was observed between all tested compounds compared to the controls (data not shown). Based on these results, it can be hypothesized that the LMW OS-EPS derivatives (GYS4 and GYS8) exert their activities through an indirect effect requiring the release of a second biological messenger. These data are in agreement with those obtained with an OS-EPS 24 kDa on osteoblastic cells (Ruiz Velasco et al., Glycobiology, 2011, 21: 781-795).

Cell Migration.

Figure 2:
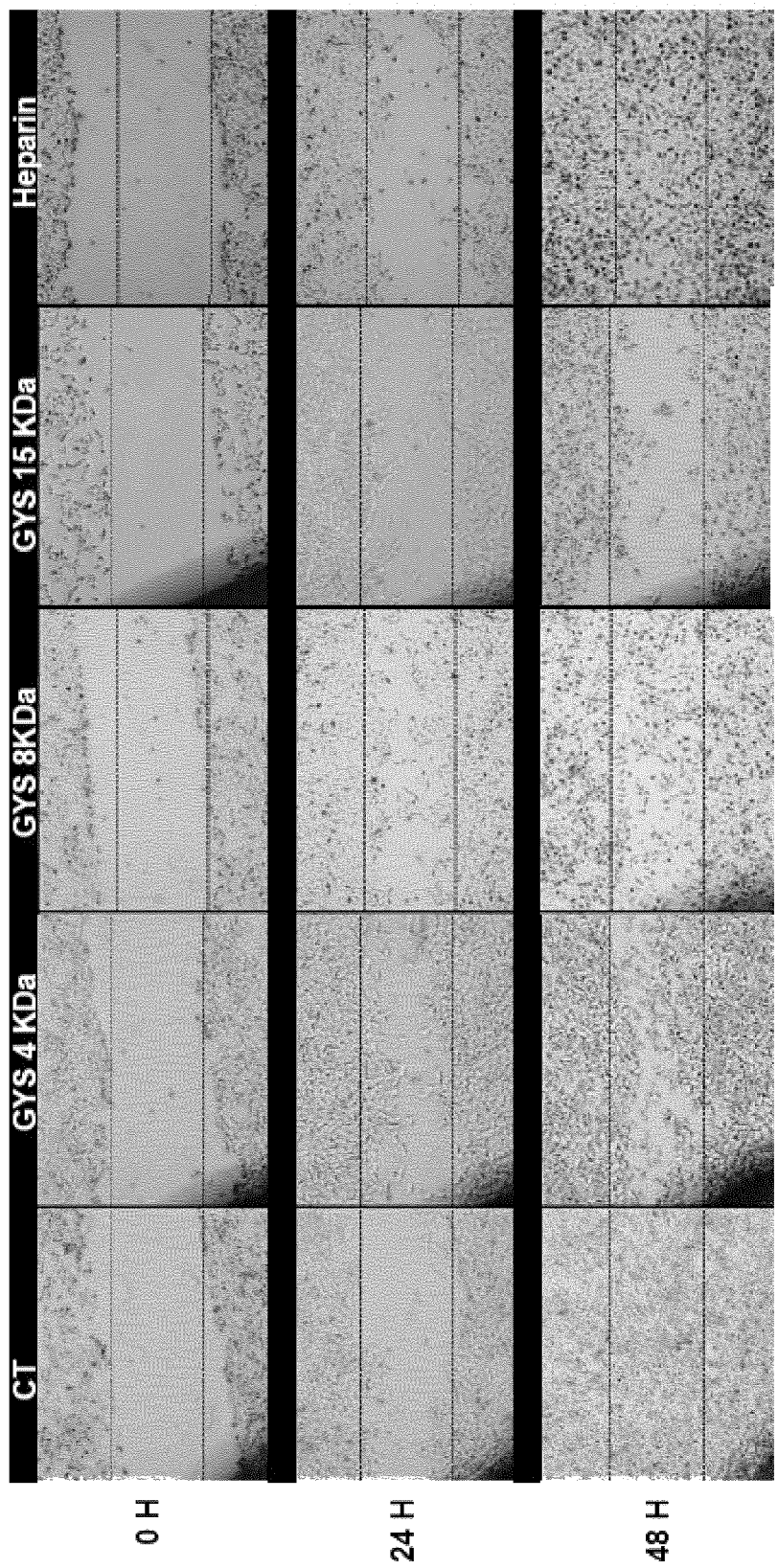
FIG. 2: Migration of cells of the human HOS cell line in the presence of different LMW OS-EPS derivatives (300 µg/ml): OS-EPS 15 kDa (GYS15), OS-EPS 8 kDa (GYS8), OS-EPS 4 kDa (GYS4), heparin (Hep) and control (CT).

The present Inventors have investigated the effects of the LMW OS-EPS derivatives on the osteosarcoma cell migration by using an in vitro wound-healing assay. All compounds assessed (GYS4, GYS8, GYS15 and heparin) were found to inhibit the migration of murine POS-1 osteosarcoma cells (data not shown). In contrast to this cell line, only GYS4 and GYS15 exhibited the ability to inhibit the migration of human HOS osteosarcoma cells (FIG. 2), in particular GYS15 was found to strongly slow down the migration of HOS cells compared to the other compounds.

It is admitted that heparin, which is generally administered as an anticoagulant, has a variety of additional biological activities especially on cancer cells (Laubli et al., Cancer Invest., 2009, 27: 474-481; Falanga et al., Semin. Thromb. Hemost., 2007, 33: 688-694). In vitro and in vivo experimental evidence demonstrated that heparin is an efficient inhibitor of cell migration, adhesion and metastasis (Laubli et al., Cancer Invest., 2009, 27: 474-481). Common molecular pathways with platelet-tumor cell thrombi formation such as the inhibition of heparanase or P-/L-selectin may be involved in this activity (Fritze et al., Biochem. Pharmacol., 2006, 72: 474-485). In contrast to heparin, the LMW OS-EPS derivatives assessed in the present work inhibited the cell migration of osteosarcoma, suggesting a mechanism of action that is independent of heparanase and selectin. Mechanisms associating inhibition of integrin activity can be hypothesized (Kapp et al., Expert Opin. Ther. Pat., 2013, 23: 1273-1295).

Cell Invasion.

Contrary to the other compounds, only GYS15 was found to inhibit the invasiveness of osteosarcoma cells with an inhibition rate close to 90% after 24 hours (FIG. 3A). This effect was observed for both the mouse POS-1 cell line and the human HOS cell line at a concentration of 25 µg/mL (FIG. 3B).

Cell Cycle.

Figure 4:
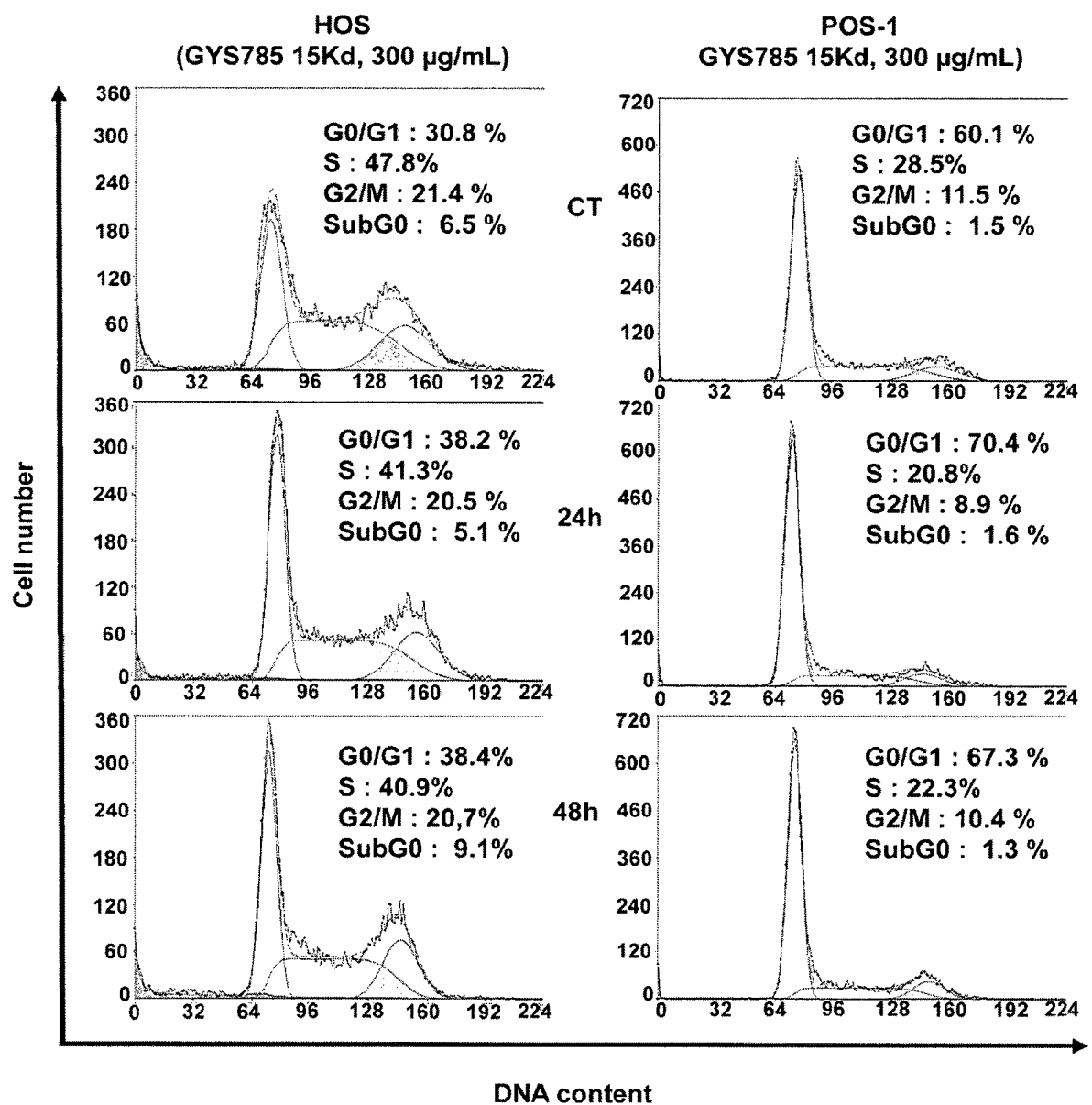
FIG. 4: Effect of the LMW OS-EPS 15 kDa derivative (GYS15) (300 µg/ml) on the cell cycle of osteosarcoma cell lines. Cell cycle distribution of human HOS and mouse POS-1 cells were studied by flow cytometry after 24 hours or 48 hours of treatment with GYS15.

At the concentration of 300 µg/ml, GYS15 had no significant effect on the cell cycle of both the mouse POS-1 and human HOS cell lines (FIG. 4). Heparin had no effects on the cell cycle at the same concentration (data not shown). Similar data were obtained after 72 hours of treatment (data not shown).

Expression in Human Osteosarcoma (HOS) Cell Line of Matrix Metalloproteinases (MMPs) and their Inhibitors (TIMPs)

Figure 5:
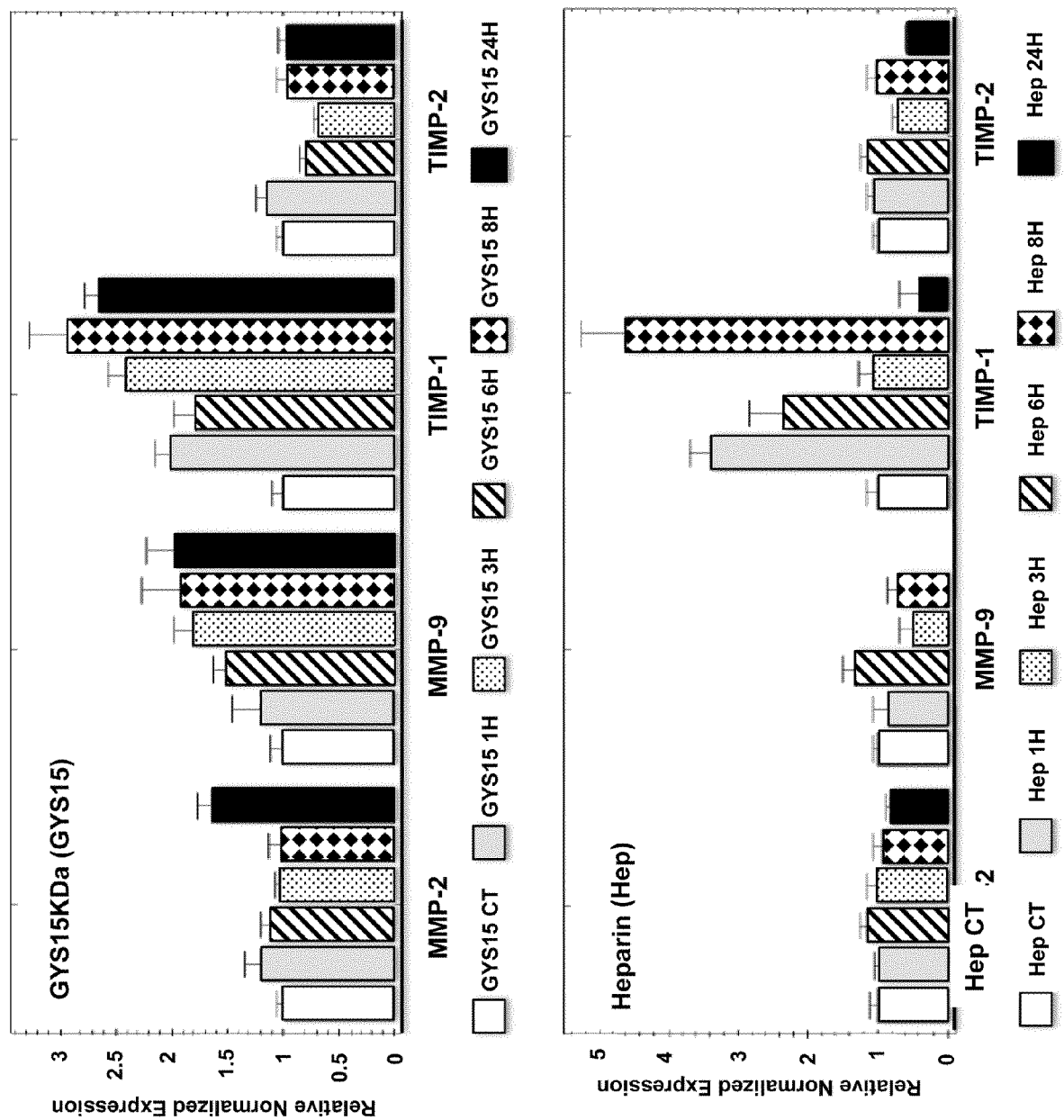
FIG. 5: Effect of the LMW OS-EPS 15 kDa derivative (GYS15) on the expression of MMP-2 and MMP-9 and their inhibitors (TIMP-1 and TIMP-2) compared to heparin in cells of the human HOS cell line. The osteosarcoma cells were treated 1 hour, 3 hours, 6 hours, 8 hours or 24 hours with GYS15 or heparin at a concentration of 50 µg/ml or with PBS (control). The cell expression of MMPs and their inhibitors in the supernatant of osteosarcoma cells was determined by quantitative polymerase chain reaction (qPRC).

Since GYS15 was found to modulate human HOS osteosarcoma cell migration and invasion, the present Inventors analyzed the expression of the main key regulators of these processes, especially MMPs and their TIMP inhibitors. As expected, human HOS osteosarcoma cells expressed MMP-2, MMP-9 as well as their inhibitors TIMP-1 and TIMP-2 (FIG. 5). MMP-2 and its inhibitor (TIMP-2) were not modulated by the treatment with GYS15 or with heparin. In contrast, MMP-9 expression was increased by GYS15 in a time-dependent manner. Indeed, 50 µg/ml of GYS15 induced a two-fold increase of MMP-9 mRNA expression compared to the untreated cells (FIG. 5). Simultaneously, GYS15 was found to up-modulate the expression of TIMP-1, which is a natural inhibitor of MMP-9 activity. Heparin only modulated the expression of TIMP-1 (FIG. 5).

Whether MMP-9 is linked to the migration, proliferation and invasiveness of osteosarcoma cells (Zhang et al., Int. Immunopharmacol., 2015, 24: 50-58; Ma et al., Eur. Rev. Med. Pharmacol. Sci., 2013, 17: 1102-1109), the use of MMP-9 as biomarker of survival in patients with osteosarcoma remains controversial (Li et al., Tumour Biol., 2014, 5: 5487-5491; Zhang et al., Tumour Biol., 2015, 36: 35: 5-6). Nevertheless, the anti-invasion and anti-migration properties of GYS15 can be partly explained by the modulation of the balance between MMP-9 and its inhibitor TIMP-1 (Cottam and Rees, Int. J. Oncol., 1993, 2: 861-872). GYS15 increased both MMP-9 and TIMP-1; however the resulting balance between the enzyme and its inhibitor is in favor of the inhibition.

In Vivo Studies

Figure 6:
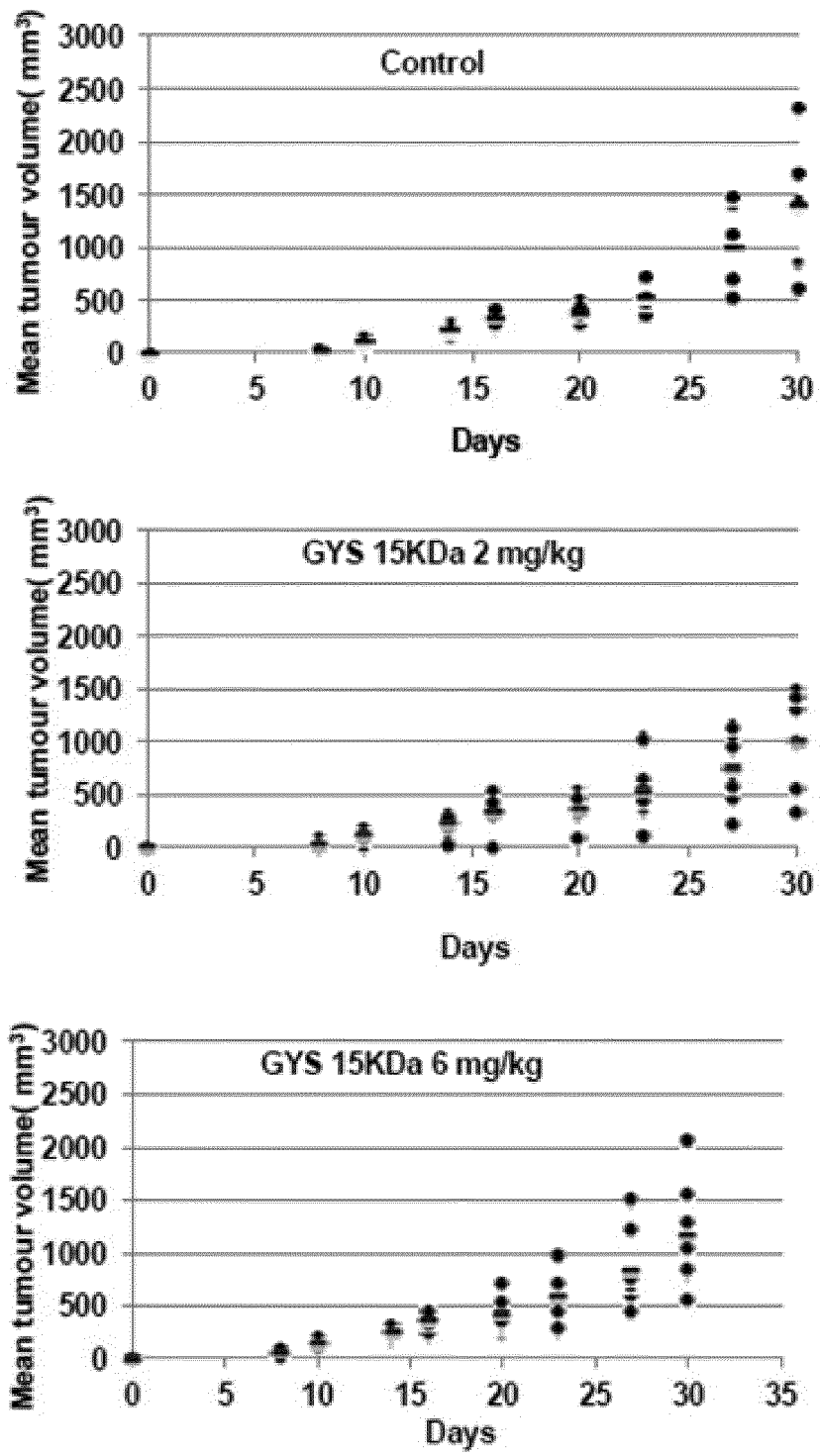
FIG. 6: Effect of the LMW OS-EPS 15 kDa derivative (GYS15) on the in vivo HOS osteosarcoma tumor growth. $22 \times 10^6$ HOS cells were inoculated in the paratibial area of a mouse model. When the tumor volume reached 100 mm$^3$, GYS15 (2 mg/kg daily or 6 mg/kg daily) was injected subcutaneously each day and the tumor growth was measured from Day 5 to Day 35.

Primary Malignant Bone Tumor Growth. A curative treatment was performed on a mouse model (paratibial model) of osteosarcoma induced by inoculation with cells of the mouse POS-1 cell line or of the human HOS cell line. The treatment started when the tumor volume reached 100 mm$^3$ (Day 0) and the mice were divided in 3 groups: 1—treated with PBS (control); 2—treated with GYS15 and 3—treated with heparin. The polysaccharides were injected subcutaneously (50 µL) each day at 2 mg/kg or 6 mg/kg and the tumor growth was measured from Day 5 to Day 9. The tumor growth was similar in the 3 groups (data not shown). These results demonstrate that both GYS15 and heparin had no effect on the primary osteosarcoma tumor induced by either the mouse POS-1 cell line (data not shown) or the human HOS cell line (FIG. 6). Both polysaccharides were not able to inhibit primary tumor growth in preclinical osteosarcoma mouse models. GYS15 had no pro-apoptotic effect on osteosarcoma cells as analyzed by a terminal deoxynucleotidyl transferase dUTP nick end labeling staining (TUNEL) (data not shown).

Model of Lung Metastases from Mouse Osteosarcoma.

Figure 7C:
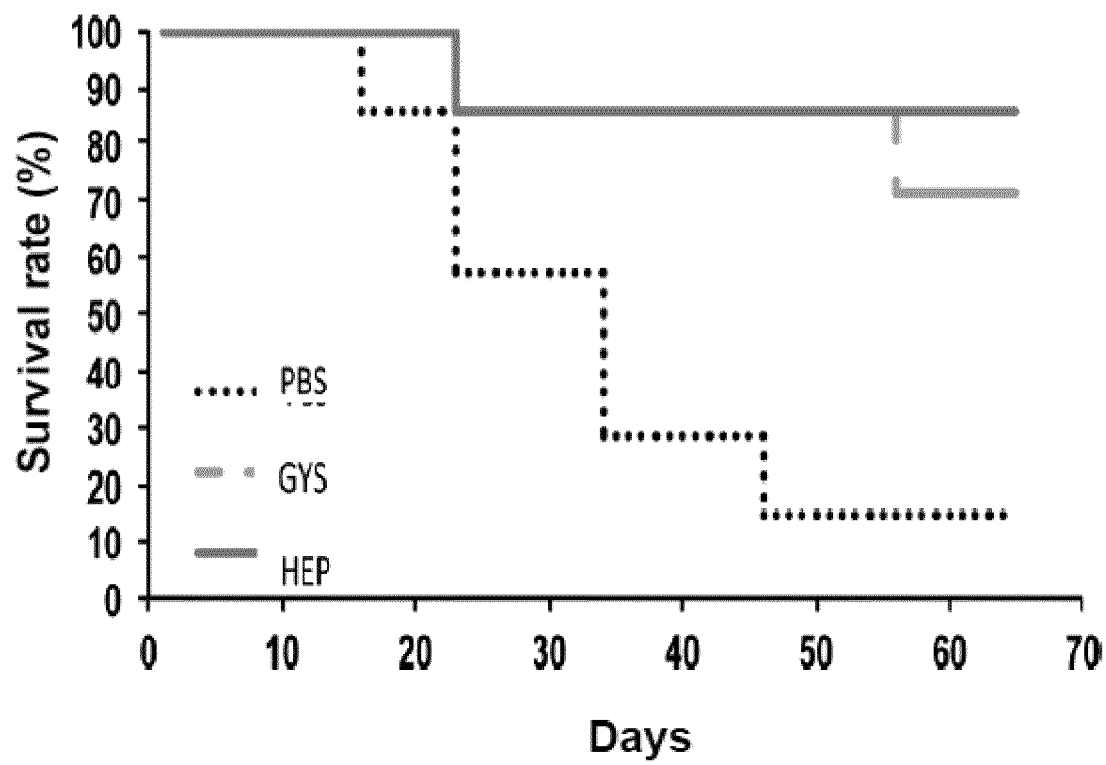
FIG. 7: Effect of the LMW OS-EPS 15 kDa derivative (GYS15) on the lung metastatic incidence. (A) Metastatic incidence in treated animals (GYS15 or heparin; s.c. 6 mg/kg daily) versus control (PBS) in percentage. (B) Histological analyses of the lung tissue of treated animals or control animals (* metastatic foci), original magnification: ×400. (C) Survival rate (%) of treated animals (GYS15 or heparin) compared to the control group (PBS), Kaplan-Meier survival curves. N=7 mice/group; $p<0.05$; $p<0.001$.

A preventive treatment was conceived to study the effect of GYS15 on the metastatic ability of osteosarcoma by the technique of retro-orbital injection of the venous sinus in mice (Cottam and Rees, Int. J. Oncol., 1993, 2: 861-872). In this experiment, mice received POS-1 cells, metastases arising spontaneously after POS-1 cell line injection. GYS15-treated mice exhibited significantly less metastases (a decrease of around 40%) than the untreated mice or heparin treated ones (p<0.001) (FIG. 7A). The histological analyses of lung tissue showed that GYS15-treated mice did not exhibit the presence of metastatic foci similarly to heparin in contrast to the control group treated with a vehicle (PBS) (FIG. 7C). This lower incidence of detectable lung metastases was accompanied by an improvement of animal survival rate, 70% of treated animals survived 65 days after the POS-1 cell line injection whereas in control group only 14% of the animals survived that long (FIG. 7C). As expected, heparin decreased the incidence of lung metastatic incidence (Laubli et al., Cancer Invest., 2009, 27: 474-481;

Falanga et al., Semin. Thromb. Hemost., 2007, 33: 688-694). No adverse effects of GYS15 were observed in mice. Therefore, GYS15 exhibits anti-metastatic activity and its low efficiency in clotting assays (Roger et al., Carbohydr. Res., 2004, 339: 2371-2380; Ruiz Velasco et al., Glycobiology, 2011, 21: 781-795), is clearly an added therapeutic value.

CONCLUSIONS

In the present study, the therapeutic interest of three over-sulfated low molecular weight marine bacterial exopolysaccharides was demonstrated. With their low efficiency in clotting assays and their ability to reduce the in vitro invasiveness of osteosarcoma cells as well as the metastatic process, LMW OS-EPSs represent a new class of polysaccharides with high interest in oncology. In the present study, only GYS15 was able to effectively inhibit both migration and invasiveness of osteosarcoma cells in vitro. Moreover, GYS15 was found to be very efficient at inhibiting the formation of lung metastases in vivo.

Such polysaccharides could also be useful to develop new delivery systems for conventional chemotherapeutic agents, even if their mechanism of action is not yet known (Arpicco et al., Molecules, 2014, 19: 3193-3230).

Throughout this application, various references describe the state of the art to which this invention pertains. The disclosures of these references are hereby incorporated by reference into the present disclosure.

The invention claimed is:

1. A method for inhibiting osteosarcoma-induced metastases formation in an osteosarcoma patient, comprising a step of administering to said osteosarcoma patient a therapeutically effective amount of a 15 kDa over-sulfated exopolysaccharide, wherein said 15 kDa over-sulfated exopolysaccharide is obtained by a method comprising the following steps:
  (a) a step consisting of free-radical depolymerization of a marine native exopolysaccharide (EPS) from the strain GY785 of the *Alteromonas* genus so as to obtain a depolymerized EPS having a molecular weight of 5,000 to 100,000 g/mol;
  (b) a subsequent step consisting of sulfation of the depolymerized EPS to obtain an over-sulfated depolymerized EPS, comprising adding to the depolymerized EPS at least one sulfation agent in an amount sufficient to obtain a sulfated polysaccharide having a degree of sulfate-group substitution of between 10% and 45% by weight relative to the total weight of the over-sulfated depolymerized EPS; and
  (c) a subsequent step consisting of isolating the 15 kDa over-sulfated exopolysaccharide (GYS15) from the over-sulfated depolymerized EPS.

2. The method according to claim 1, wherein the step of isolating GYS15 from the over-sulfated depolymerized EPS is carried out by fractionation.

3. The method according to claim 1, wherein the osteosarcoma patient is suffering from osteosarcoma, or has previously undergone therapy for osteosarcoma.

4. The method according to claim 1, wherein the osteosarcoma patient is undergoing therapy for osteosarcoma.

5. The method according to claim 1, wherein the 15 kDa over-sulfated exopolysaccharide is administered as a pharmaceutical composition.

6. The method according to claim 2, wherein the fractionation is performed by size exclusion chromatography.

7. The method according to claim 1, wherein the method is for inhibiting osteosarcoma-induced metastases formation in a lung of the osteosarcoma patient.

* * * * *